US010709383B2

(12) United States Patent
Morris et al.

(10) Patent No.: US 10,709,383 B2
(45) Date of Patent: Jul. 14, 2020

(54) WRIST-WORN PULSE TRANSIT TIME SENSOR

(71) Applicant: Microsoft Technology Licensing, LLC, Redmond, WA (US)

(72) Inventors: Daniel Morris, Bellevue, WA (US); Desney S. Tan, Kirkland, WA (US); T. Scott Saponas, Woodinville, WA (US); Shwetak N. Patel, Seattle, WA (US); Nicolas Villar, Cambridge (GB); Gregory R. Smith, Bellevue, WA (US); Sidhant Gupta, Seattle, WA (US); Gabriel Adam Cohn, Sammamish, WA (US); David C. Kale, Los Angeles, CA (US); Sailaja Malladi, Kirkland, WA (US); Ronald E. Paulsen, Woodinville, WA (US)

(73) Assignee: MICROSOFT TECHNOLOGY LICNESING, LLC, Redmond, WA (US)

( * ) Notice: Subject to any disclaimer, the term of this patent is extended or adjusted under 35 U.S.C. 154(b) by 769 days.

(21) Appl. No.: 14/750,646

(22) Filed: Jun. 25, 2015

(65) Prior Publication Data
US 2016/0287172 A1 Oct. 6, 2016

Related U.S. Application Data (60) Provisional application No. 62/142,441, filed on Apr. 2, 2015.

(51) Int. Cl.
*A61B 5/00* (2006.01)
*A61B 5/024* (2006.01)
(Continued)

(52) U.S. Cl.
CPC ............ *A61B 5/681* (2013.01); *A61B 5/0024* (2013.01); *A61B 5/0077* (2013.01); *A61B 5/022* (2013.01);
(Continued)

(58) Field of Classification Search
CPC ........... A61B 5/742; A61B 7/04; A61B 5/029; A61B 5/681; A61B 5/022; A61B 5/11;
(Continued)

(56) References Cited

U.S. PATENT DOCUMENTS

| 4,256,117 A | 3/1981 | Perica et al. |
| 4,409,983 A | 10/1983 | Albert |

(Continued)

FOREIGN PATENT DOCUMENTS

| CN | 1325285 A | 5/2001 |
| CN | 1849998 A | 10/2006 |

(Continued)

OTHER PUBLICATIONS

Newlin et al., Pre-ejection Period: Measuring Beta-adrenergic Influences Upon the Heart, 1979, Psychophysiology, vol. 16, No. 6, p. 546-553 (Year: 1979).*

(Continued)

*Primary Examiner* — Michael R Bloch
(74) *Attorney, Agent, or Firm* — Alleman Hall Creasman & Tuttle LLP (57) ABSTRACT

A wrist-worn device heart-monitoring device is presented. The wrist-worn heart-monitoring device includes a radial tonometer configured to output a pressure signal indicating a pulse pressure wave at a user's wrist, two or more electrodes configured to output an electrical signal indicating a user's heart has been commanded to contract, and a microphone configured to output an audio signal indicating a closing of a user's aortic valve. The wrist-worn heart- (Continued)

monitoring device further includes a pulse transit time monitor configured to calculate a pre-ejection period of the user's heart based on at least the pressure, electrical, and audio signals, and calculate a pulse transit time based on at least the pre-ejection period, the pressure signal, and the electrical signal.

10 Claims, 7 Drawing Sheets

(51) Int. Cl.
*A61B 5/0245* (2006.01)
*A61B 5/02* (2006.01)
*A61B 5/0205* (2006.01)
*A61B 5/021* (2006.01)
*A61B 5/022* (2006.01)
*A61B 5/029* (2006.01)
*A61B 5/0408* (2006.01)
*A61B 5/107* (2006.01)
*A61B 5/11* (2006.01)
*A61B 7/04* (2006.01)

(52) U.S. Cl.
CPC ............ *A61B 5/024* (2013.01); *A61B 5/0205* (2013.01); *A61B 5/029* (2013.01); *A61B 5/02028* (2013.01); *A61B 5/0245* (2013.01); *A61B 5/02125* (2013.01); *A61B 5/02444* (2013.01); *A61B 5/04085* (2013.01); *A61B 5/1072* (2013.01); *A61B 5/1075* (2013.01); *A61B 5/11* (2013.01); *A61B 5/6831* (2013.01); *A61B 5/7264* (2013.01); *A61B 5/7278* (2013.01); *A61B 5/742* (2013.01); *A61B 5/7475* (2013.01); *A61B 7/04* (2013.01); *A61B 5/02438* (2013.01); *A61B 5/6824* (2013.01); *A61B 5/6828* (2013.01); *A61B 2560/0462* (2013.01); *A61B 2560/0468* (2013.01); *A61B 2562/0247* (2013.01)

(58) Field of Classification Search
CPC ... A61B 5/1072; A61B 5/7264; A61B 5/7278; A61B 5/0024; A61B 5/1075; A61B 5/02125; A61B 5/04085; A61B 5/0245; A61B 5/0244
See application file for complete search history.

(56) References Cited

U.S. PATENT DOCUMENTS

| | | | |
|---|---|---|---|
| 4,802,488 A | 2/1989 | Eckerle | |
| 5,289,824 A | 3/1994 | Mills et al. | |
| 8,700,137 B2 | 4/2014 | Albert | |
| 8,708,923 B2 | 4/2014 | Turicchia et al. | |
| 8,747,336 B2 | 6/2014 | Tran | |
| 2002/0177781 A1* | 11/2002 | Amano | A61B 5/021 600/485 |
| 2002/0193691 A1* | 12/2002 | Sato | A61B 5/02125 600/495 |
| 2003/0220577 A1 | 11/2003 | Bartels et al. | |
| 2004/0167409 A1 | 8/2004 | Lo et al. | |
| 2007/0100244 A1 | 5/2007 | Lin | |
| 2008/0266118 A1 | 10/2008 | Pierson et al. | |
| 2009/0054751 A1 | 2/2009 | Babashan et al. | |
| 2010/0069735 A1* | 3/2010 | Berkner | A61B 5/04028 600/382 |
| 2010/0076331 A1 | 3/2010 | Chan et al. | |
| 2010/0228311 A1 | 9/2010 | Naqvi et al. | |
| 2012/0283583 A1 | 11/2012 | Batkin et al. | |
| 2013/0345540 A1 | 12/2013 | Salazar et al. | |
| 2014/0148715 A1* | 5/2014 | Alexander | A61B 5/6898 600/509 |
| 2014/0221854 A1 | 8/2014 | Wai | |
| 2014/0249398 A1 | 9/2014 | Morris et al. | |
| 2014/0275852 A1 | 9/2014 | Hong et al. | |
| 2014/0300490 A1 | 10/2014 | Katz et al. | |
| 2015/0374244 A1* | 12/2015 | Yoo | A61B 5/0285 600/485 |
| 2016/0206277 A1* | 7/2016 | Bidichandani | A61B 7/04 |
| 2017/0340209 A1* | 11/2017 | Klaassen | A61B 5/681 |

FOREIGN PATENT DOCUMENTS

| | | |
|---|---|---|
| CN | 101247757 A | 8/2008 |
| CN | 102113034 A | 6/2011 |
| CN | 202211686 U | 5/2012 |
| CN | 103491868 A | 1/2014 |
| CN | 103919536 A | 7/2014 |
| CN | 104173035 A | 12/2014 |
| CN | 104244814 A | 12/2014 |
| KR | 101349767 B1 | 1/2014 |
| KR | 101485700 B1 | 1/2015 |
| KR | 1020150092465 A | 8/2015 |
| KR | 1020160092250 A | 8/2016 |
| KR | 101667412 B1 | 10/2016 |
| WO | 2014089665 A1 | 6/2014 |
| WO | 2014123345 A1 | 8/2014 |
| WO | 2014172451 A1 | 10/2014 |
| WO | 2015030712 A1 | 3/2015 |

OTHER PUBLICATIONS

Mandal, et al., "A Battery-Free Tag for Wireless Monitoring of Heart Sounds", In Proceedings of Sixth International Workshop on Wearable and Implantable Body Sensor Networks, Jun. 3, 2009, pp. 201-206.
Poh, et al., "Cardiovascular Monitoring Using Earphones and a Mobile Device", In Pervasive Computing, Oct. 2012, 9 pages.
U.S. Appl. No. 61/927,796, Saponas, et al., "Chair That Senses Cardiovascular Risk Factors", filed Jan. 15, 2014.
U.S. Appl. No. 14/500,029, Villar, et al., "Wearable Sensing Band", filed Sep. 29, 2014.
IPEA European Patent Office, International Preliminary Report on Patentability Issued in PCT Application No. PCT/US2016/025459, dated Mar. 3, 2017, WIPO, 8 Pages.
"H2: The First Wearable Blood Pressure Monitor", Indiegogo Website, Available Online at https://www.indiegogo.com/projects/h2-the-first-wearable-blood-pressure-monitor#/, Available as Early as Oct. 31, 2014, 32 pages.
Buxi, D. et al., "A survey on signals and systems in ambulatory blood pressure monitoring using pulse transit time", Institute of Physics and Engineering in Medicine, Physiological Measurement, vol. 36, Issue 3, Feb. 19, 2015, 26 pages.
ISA European Patent Office, International Search Report and Written Opinion Issued in PCT Application No. PCT/US2016/025459, dated Sep. 13, 2016, WIPO, 19 pages.
"Office Action Issued in European Patent Application No. 16716391.4", dated Sep. 5, 2018, 4 Pages
"First Office Action and Search Report Issued in Chinese Patent Application No. 201680021012.X", dated Nov. 4, 2019, 13 Pages.

* cited by examiner

WRIST-WORN PULSE TRANSIT TIME SENSOR

CROSS REFERENCE TO RELATED APPLICATIONS

This application claims priority to U.S. Provisional Patent Application No. 62/142,441, filed Apr. 2, 2015, the entirety of which is hereby incorporated herein by reference.

BACKGROUND

Monitoring cardiovascular system metrics provides useful health information. Conventional cardiovascular monitoring equipment is designed to be used by trained professionals in a clinical setting.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

A wrist-worn heart-monitoring device is presented. The wrist-worn heart-monitoring device includes a radial tonometer configured to output a pressure signal indicating a pulse pressure wave at a wearer's wrist, two or more electrodes configured to output an electrical signal indicating a wearer's heart has been commanded to contract, and a microphone configured to output an audio signal indicating a closing of a wearer's aortic valve. The wrist-worn heart-monitoring device further includes a pulse transit time monitor configured to calculate a pre-ejection period of a wearer's heart based on at least the pressure, electrical, and audio signals, and calculate a pulse transit time based on at least the pre-ejection period, the pressure signal, and the electrical signal.

DETAILED DESCRIPTION

Heart disease is the leading cause of death in the United States, accounting for around six hundred thousand deaths in 2011 alone (nearly 31% of reported deaths in the United States). For many cardiovascular conditions, preventative monitoring can significantly improve outcomes, as can continuous monitoring after treatment. However, most monitoring methods are prohibitively cumbersome. Rhythmic conditions are typically monitored with adhesive electrocardiogram (EKG) electrodes, which are uncomfortable and require frequent replacement. Consequently, continuous EKG monitoring is only rarely ordered for long-term observation.

Hypertension is typically monitored with periodic blood pressure measurement. However, instantaneous measurements may be error-prone and misleading. Standard methods for determining blood pressure, such as an inflatable arm cuff, are prohibitively cumbersome for consistent home use. Pulse wave velocity measurement has emerged as a potential replacement for or complement to blood pressure measurement. However, pulse wave velocity measurement currently requires two uncomfortable sensors to be pressed against a user's arteries by a trained clinical expert, with at least one of those two sensors at the often-inaccessible carotid artery in the neck.

Wrist-worn cardiovascular sensors, on the other hand, are practical and small, and may be embedded in productive and/or fashionable devices such as smartwatches and bracelets. However, wrist-worn health sensing is currently limited to simple—and relatively uninformative—metrics like heart rate. Comprehensive cardiovascular monitoring greatly benefits from at least some information gathered from the thorax.

As described below, a sensor-and-logic system can be configured to acquire cardiovascular data from both the chest and the wrist. Such a system can be integrated into a single wrist-worn device. By leveraging the relatively simple technique of touching a wrist-worn sensor to the wearer's chest, metrics such as pulse transit time that can only be computed by the combination of these two locations may be achieved in a wearable device, and may thus allow a wearer to monitor cardiovascular health frequently outside of a clinical setting.

Figure 1:
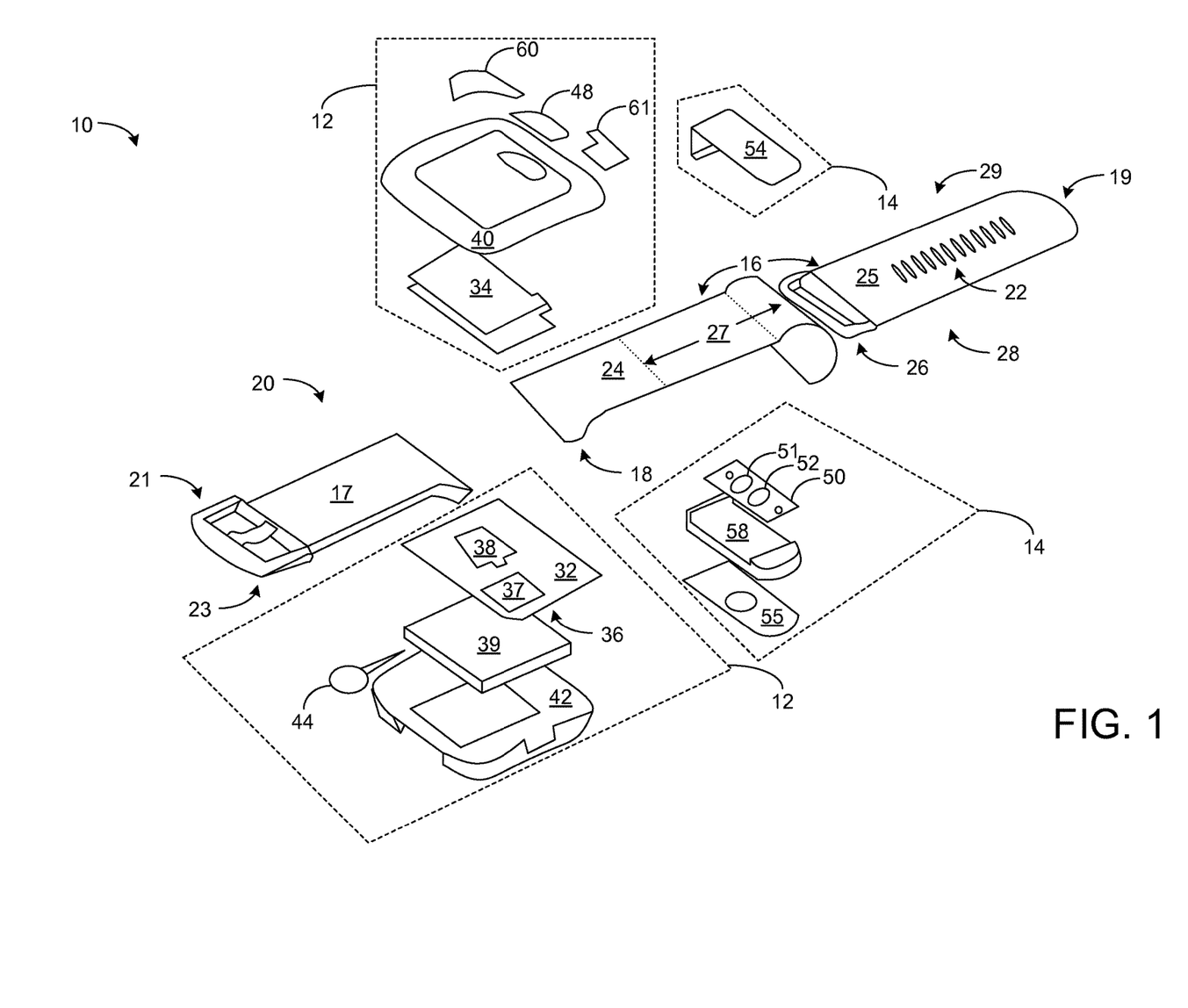
FIG. 1 shows an exploded view of a wearable electronic device.

FIG. 1 shows aspects of an example sensor-and-logic system in the form of a wearable electronic device 10. The wearable electronic device 10 may be configured to measure, analyze, and/or report one or more health/fitness parameters of a wearer of wearable electronic device 10. Wearable electronic device 10 is not limiting. One or more of the features described below with reference to wearable electronic device 10 may be implemented in another sensor-and-logic system, which optionally may have a form factor that differs from wearable electronic device 10.

Wearable electronic device 10 is shown disassembled in order to depict inner componentry. The illustrated device is band-shaped and may be worn around a wrist. Wearable electronic device 10 includes a primary device 12 and a satellite device 14. Components of primary device 12 and satellite device 14 are indicated by dashed outlines. Primary device 12 may have a form function similar to the main body of a watch, and may comprise the primary user interface componentry (e.g., display, inputs, etc.) for wearable electronic device 10. Satellite device 14 may comprise pulse pressure wave transduction componentry that may enable wearable electronic device 10 to function as a wearable cardiovascular monitoring device. The accuracy of pulse pressure wave transduction may be dependent on the placement of the transduction componentry relative to the wearer's skin and underlying tissue and vasculature. For example, including the pulse pressure wave transduction componentry in satellite device 14 may enable pulse pressure wave transduction at the underside of the wearer's wrist while primary device 12 is situated on the back of the wearer's wrist in a position that is familiar to watch-wearers.

Wearable electronic device 10 is shown having a first strap 16 and a second strap 17. However, in some examples a single strap may be included, and in some examples, more than two straps may be included. The straps of wearable electronic device 10 may be elastomeric in some examples, and one or more of the straps optionally may be comprised of a conductive elastomer. First strap 16 may be connected to primary device 12 at first end 18, while second end 19 is located on the opposite, distal end of first strap 16. Similarly, second strap 17 may be connected to primary device 12 at first end 20, while second end 21 is located on the opposite, distal end of second strap 17. First strap 16 comprises primary fastening componentry 22 located towards second end 19, while second strap 17 comprises secondary fastening componentry 23 located towards second end 21. The straps and fastening componentry enable wearable electronic device 10 to be closed into a loop and to be worn on a wearer's wrist.

In this example, first strap 16 comprises a proximal portion 24 which connects to primary device 12 and a distal portion 25 that comprises primary fastening componentry 22. Proximal portion 24 and distal portion 25 may be coupled together via tertiary fastening componentry 26. In this way the distance between primary device 12 and primary fastening componentry 22 may be adjusted. However, in other examples, first strap 16 may be a single continuous strap that both connects to primary device 12 and comprises primary fastening componentry 22.

Satellite device 14 may be attached to first strap 16 at a fixed position within attachment region 27 of first strap 16, thus establishing a fixed distance between primary device 12 and satellite device 14. Primary fastening componentry 22 and secondary fastening componentry 23 are complementary, and thus may be adjustably engaged to adjust the circumference of wearable electronic device 10 without moving the fixed position of satellite device 14 relative to primary device 12. In this example, primary fastening componentry 22 includes discrete locations for engaging with secondary fastening componentry 23. However, in other examples, primary fastening componentry 22 and secondary fastening componentry 23 may be adjustably engaged along a continuous region.

Wearable electronic device 10 comprises a user-adjacent side 28 and an externally facing side 29. As such, primary device 12, satellite device 14, first strap 16, and second strap 17 may each have a user-adjacent side and externally facing side. In the closed conformation, wearable electronic device 10 thus comprises an inner surface (user-adjacent) and an outer surface (externally facing).

Wearable electronic device 10 includes various functional components integrated into primary device 12. In particular, primary device 12 includes a compute system 32, display 34, communication suite 36, and various sensors. These components draw power from one or more energy-storage cells 39. A battery—e.g., a lithium ion battery—is one type of energy-storage cell suitable for this purpose. Examples of alternative energy-storage cells include super- and ultra-capacitors. In wearable electronic devices worn on the wearer's wrist, the energy-storage cells may be curved to fit the wrist.

In general, energy-storage cells 39 may be replaceable and/or rechargeable. In some examples, recharge power may be provided through a universal serial bus (USB) port, which may include a magnetic latch to releasably secure a complementary USB connector. In other examples, the energy-storage cells 39 may be recharged by wireless inductive or ambient-light charging. In still other examples, the wearable electronic device 10 may include electro-mechanical componentry to recharge the energy-storage cells 39 from the wearer's adventitious or purposeful body motion. For example, batteries or capacitors may be charged via an electromechanical generator integrated into wearable electronic device 10. The generator may be turned by a mechanical armature that turns while the wearer is moving and wearing wearable electronic device 10.

Within primary device 12, compute system 32 is situated below display 34 and operatively coupled to display 34, along with communication suite 36, and various sensors. The compute system 32 includes a data-storage machine 37 to hold data and instructions, and a logic machine 38 to execute the instructions. Aspects of compute system 32 are described in further detail with reference to FIG. 9. These components may be situated within primary device 12 between top device housing frame 40 and bottom device housing frame 42. Primary device 12 may further comprise other actuators that may be utilized to communicate with the wearer, such as haptic motor 44, and/or a loudspeaker (not shown).

Display 34 may be any suitable type of display. In some configurations, a thin, low-power light emitting diode (LED) array or a liquid-crystal display (LCD) array may be used. An LCD array may be backlit in some implementations. In other implementations, a reflective LCD array (e.g., a liquid crystal on silicon, (LCOS) array) may be frontlit via ambient light. A curved display may also be used. Further, active-matrix organic light-emitting diode (AMOLED) displays or quantum dot displays may be used.

Communication suite 36 may include any appropriate wired or wireless communication componentry. In some examples, the communication suite 36 may include a USB port, which may be used for exchanging data between wearable electronic device 10 and other computer systems, as well as providing recharge power. The communication suite 36 may further include two-way Bluetooth, Wi-Fi, cellular, near-field communication and/or other radios. In some implementations, communication suite 36 may include an additional transceiver for optical (e.g., infrared) communication.

In wearable electronic device 10, a touch-screen sensor may be coupled to display 34 and configured to receive touch input from the wearer. The touch-screen sensor may be resistive, capacitive, or optically based. Pushbutton sensors may be used to detect the state of push button 48, which may include rockers. Input from the pushbutton sensor may be used to enact a home-key or on-off feature, control audio volume, turn a microphone on or off, etc.

Wearable electronic device 10 may include a plurality of additional sensors. Such sensors may include one or more microphones, visible-light sensors, ultraviolet sensors, and/or ambient temperature sensors. A microphone may provide input to compute system 32 that may be used to measure the ambient sound level or receive voice commands from the wearer. Input from the visible-light sensor, ultraviolet sensor, and ambient temperature sensor may be used to assess aspects of the wearer's environment—i.e., the temperature, overall lighting level, and whether the wearer is indoors or outdoors.

A secondary compute system 50 is located within satellite device 14. Secondary compute system 50 may include a data-storage machine 51 to hold data and instructions, and a logic machine 52 to execute the instructions. Secondary compute system 50 may be situated between top satellite housing frame 54 and bottom satellite housing frame 55. Top satellite housing frame 54 and bottom satellite housing frame 55 may be configured to couple satellite device 14 to a fixed position within attachment region 27 on first strap 16 through the use of screws, bolts, clamps, etc. Top satellite housing frame 54 and bottom satellite housing frame 55 are shown as separate components, but in some examples, they may be coupled together by a hinge on one end, allowing satellite device 14 to be latched together around first strap 16 at the other end.

Secondary compute system 50 may be communicatively coupled to compute system 32. Satellite device 14 may mediate communication between secondary compute system 50 and compute system 32. For example, satellite device 14 may include one or more conductive contacts configured to physically intersect with one or more conductive wires extending from primary device 12 through attachment region 27 within first strap 16. In other examples, secondary compute system 50 may be coupled to compute system 32 via capacitive contact between one or more conductive contacts on satellite device 14 and one or more conductive wires within first strap 16. In other examples, a ribbon cable may extend from primary device 12 through first strap 16 such that one or more contacts on satellite device 14 can intersect with the ribbon cable when the satellite device 14 is affixed to first strap 16. In some examples, secondary compute system 50 may communicate with compute system 32 via wireless communication. In some examples, satellite device 14 may include one or more energy-storage cells. In other examples, satellite device 14 and components housed therein may draw power from energy-storage cells 39.

A pressure transducing device 58 is located within satellite device 14. When placed above the wearer's radial artery, the pressure transducing device 58 may transduce a pulse pressure wave present in the radial artery, thus functioning as a radial tonometer. The transduced pulse pressure waves may then be converted into pulse waveform signals and utilized to determine the wearer's heart rate, blood pressure, and other cardiovascular properties. Attachment region 27 may comprise a plurality of possible sensing locations, each possible sensing location having a different effective distance from primary device 12 along the first strap 16. In some examples, attachment region 27 may comprise a plurality of continuous possible sensing locations, while in other examples attachment region 27 may comprise a plurality of discrete possible sensing locations. By adjusting the distance between primary device 12 and satellite device 14, satellite device 14 and pressure transducing device 58 may be placed directly over the wearer's radial artery while primary device 12 is positioned on the back of the wearer's wrist. In some examples, satellite device 14 may be coupled to first strap 16 at a fixed position (e.g., at second end 19). In such examples, the distance between satellite device 14 and primary device 12 may be adjusted via interactions between satellite device 14 and first strap 16, via interactions between first strap 16 and primary device 12, and/or between regions of first strap 16.

Bottom satellite housing frame 55 is shown with an opening through which pressure transducing device 58 can establish contact with the wearer's wrist at the radial artery. Wearable electronic device 10 may be configured to instruct the wearer to adjust the position of satellite device 14 relative to the radial artery if a pressure detected by the pressure transducing device 58 is below a threshold, and/or if a signal quality of the transduced pressure is below a threshold. In some examples, wearable electronic device 10 may be configured to self-adjust the position of satellite device 14 and/or the overall circumference of wearable electronic device 10.

In some examples, pressure transducing device 58 may be housed and configured to interface with a wearer's wrist independently from primary device 12. For example, pressure transducing device 58 may be worn on one wrist, while primary device 12 may be worn on the other wrist. In other examples, pressure transducing device 58 may be configured to be worn while primary device 12 is not worn. Pressure transducing device 58 may thus be configured to communicate with one or more additional computing devices, (e.g., via secondary compute system 50) such as a personal computer, tablet computer, smart phone, smart watch, gaming device, etc.

FIG. 1 shows a pair of contact sensor modules 60 and 61 situated on top device housing frame 40, which may be touchable by a wearer using fingers on the hand opposite the wrist where wearable electronic device 10 is worn. In some examples, other contact sensor modules may be included in addition to or as an alternative to contact sensor modules 60 and 61. As one example, other contact modules may be attached to user-adjacent side 28 of primary device 12, first strap 16 and/or second strap 17, and thus be held in contact with points on the wearer's wrist when wearable electronic device 10 is worn. As another example, one or more contact modules may be situated at or near secondary fastening componentry 23 on the externally-facing side 29 of wearable electronic device 10 when wearable electronic device 10 is closed into a loop, thus allowing the wearer to contact a point on their body reachable with the underside of the wearer's wrist. Additionally or alternatively, one or more contact modules may be situated on the externally-facing side 29 of the loop at first strap 16 and/or second strap 17.

Contact sensor modules 60 and 61 may include independent or cooperating sensor elements, to provide a plurality of sensory functions. For example, contact sensor modules 60 and 61 may provide an electrical resistance and/or capacitance sensory function, which measures the electrical resistance and/or capacitance of the wearer's skin. Compute system 32 may use such input to assess whether or not the device is being worn, for instance. In some implementations, the sensory function may be used to determine how tightly wearable electronic device 10 is being worn. In some examples, a contact sensor module may also provide measurement of the wearer's skin temperature. In some examples, contacting multiple contact sensor modules may allow compute system 32 to determine an electrocardiogram (EKG) of the wearer.

Wearable electronic device 10 may also include motion sensing componentry, such as an accelerometer, gyroscope, and magnetometer. The accelerometer and gyroscope may furnish acceleration data along three orthogonal axes as well as rotational data about the three axes, for a combined six degrees of freedom. This sensory data can be used to provide a pedometer/calorie-counting function, for example. Data from the accelerometer and gyroscope may be combined with geomagnetic data from the magnetometer to further define the inertial and rotational data in terms of geographic orientation. The wearable electronic device 10 may also include a global positioning system (GPS) receiver for determining the wearer's geographic location and/or velocity. In some configurations, the antenna of the GPS receiver may be relatively flexible and extend into straps 16 and/or 17. In some examples, data from the motion sensing componentry may be utilized to determine a position of the wearable electronic device 10, contact modules 60 and or 61, and/or pressure transducing device 58 relative to predetermined sensing locations on the body of the device wearer.

In some examples, wearable electronic device 10 may also include one or more optical sensors paired with one or more optical sources. The optical sources may be configured to illuminate the skin and/or the underlying tissue and blood vessels of the wearer, while the optical sensors may be configured to detect illumination reflected off of the skin and/or the underlying tissue and blood vessels of the wearer. This optical data may be communicated to compute system 32, where the data may be used to determine the wearer's blood-oxygen level, pulse, blood glucose levels, or other biometric markers with optical signatures.

Compute system 32, via the sensory functions described herein, is configured to acquire various forms of information about the wearer of wearable electronic device 10. Such information must be acquired and used with utmost respect for the wearer's privacy. Accordingly, the sensory functions may be enacted subject to opt-in participation of the wearer. In implementations where personal data is collected on the device and transmitted to a remote system for processing, that data may be anonymized. In other examples, personal data may be confined to the wearable electronic device, and only non-personal, summary data transmitted to the remote system.

Recording an electrocardiogram (EKG) signal requires measuring the voltage between two points of electrical contact with the body, on opposite sides of the heart. Each physical point of contact is mediated by an electrode, i.e. the physical piece of material that makes contact with the skin. If a line is drawn between two electrodes on opposite sides of the heart, along the surface of the skin, the orientation of that line when it crosses the heart defines the lead that is being measured.

Figure 2:
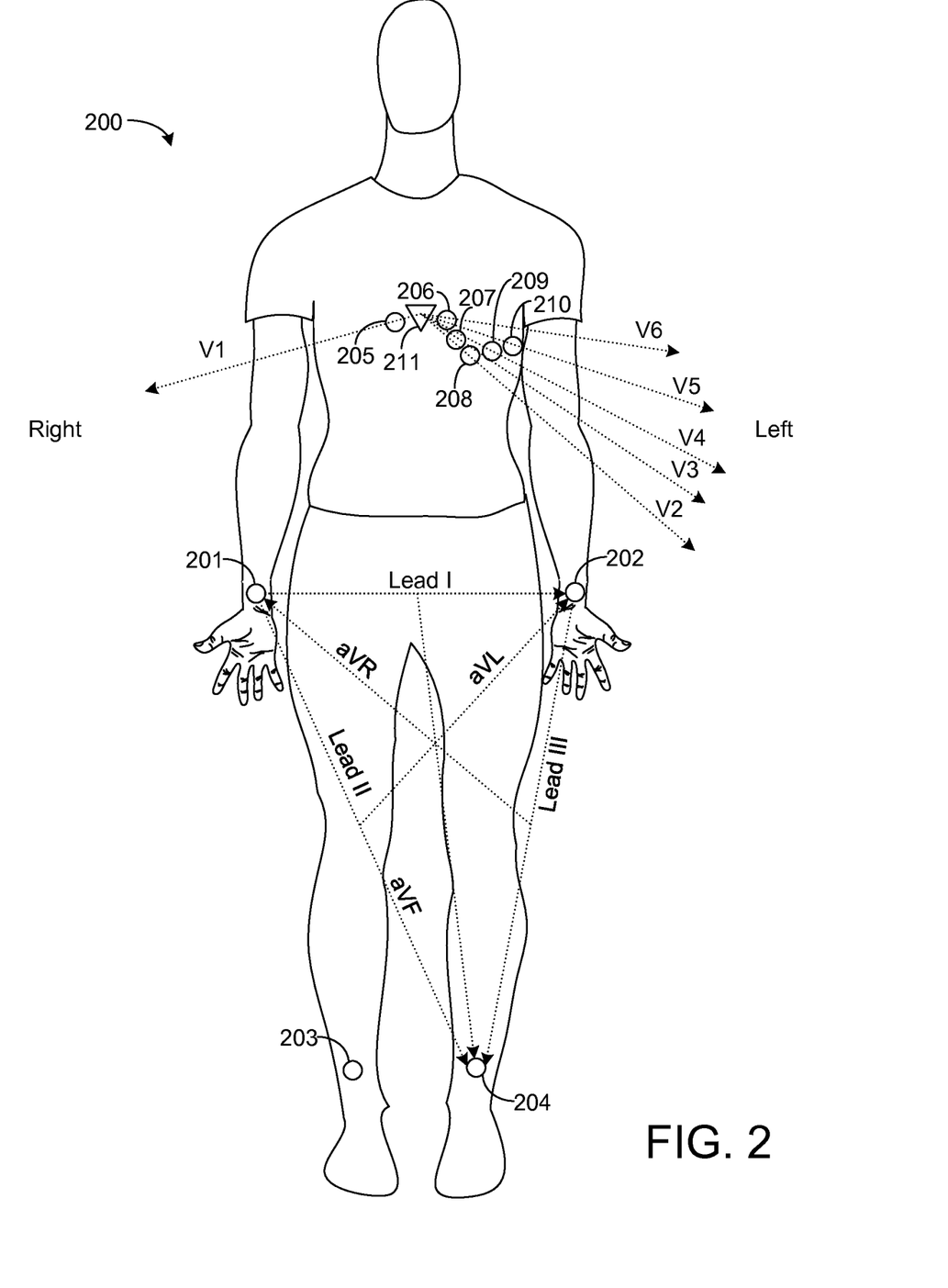
FIG. 2 shows a schematic of electrocardiogram electrode placement on a user.

FIG. 2 illustrates an example placement of 10 electrodes on a user 200 that may be utilized to record a 12 lead EKG. Electrode 201 (RA) is placed on the right arm, typically away from dense muscle tissue (e.g. forearms, shoulders). Electrode 202 (LA) is placed on the left arm in the same relative location as electrode 201. Electrode 203 (RL) is placed on the right leg, typically on the calf near the ankle, although it may be placed further up the leg. Electrode 204 (LL) is placed on the left leg, in the same relative location as electrode 203. Electrode 203 is used solely as a ground electrode.

Electrodes 205-210 are placed on the chest. Electrode 205 (V1) is placed between ribs 4 and 5 to the right of the sternum. Electrode 206 (V2) is placed between ribs 4 and 5 to the left of the sternum. Electrode 207 (V3) is placed between electrode 206 and electrode 208 (V4) which is placed between ribs 5 and 6 in the mid-clavicular line. Electrode 209 (V5) is placed horizontally even with electrode 208 in the left anterior axillary line, while electrode 210 (V6) is placed horizontally even with electrodes 208 and 209 in the mid-axillary line.

Arrows in FIG. 2 represent an electrical direction of a lead from a negative electrode to a positive electrode. Lead I is a voltage measurement made from the left arm to the right arm, i.e. along a line that crosses the heart horizontally. Lead II is a voltage measurement between the left leg and the right arm, while lead III is a voltage measurement between the left leg and the left arm. Leads I-III are bipolar leads, as they utilize two electrodes as the positive and negative poles. Together, Leads I-III are known as limb leads (also known as Einthoven's triangle) and may be used to calculate an average voltage potential across the body which may be used as a composite negative pole 211 (also known as Wilson's central terminal) which may then be used as the negative pole for unipolar leads.

For example, leads augmented vector right (aVR), augmented vector left (aVL), and augmented vector foot (aVF) are unipolar augmented limb leads, each having a positive pole at an electrode (electrodes 201, 202, and 204, respectively) and the composite negative pole. The six limb leads may be used to calculate the heart's electrical axis in the frontal plane.

Leads V1-V6 are known as precordial leads, utilizing the corresponding electrodes as positive poles for those leads, with voltages measured from the composite negative pole. Leads V1-V6 are perpendicular to the limb leads.

In clinical practice, anywhere from 1 lead to 12 leads are measured, representing different vectors across the heart. Measuring 12 leads does not require 10 electrodes. For example, 6 electrodes may be used, and different combinations of those 6 make up the 12 leads. All 12 leads may be measured with as few as two electrodes (although not simultaneously), by moving those two electrodes around between measurements.

When the heart pumps, it sends a pressure wave traveling along the arterial tree, which forces oxygenated blood out to tissues. This pressure wave takes time to propagate. For example, the pressure wave at the wrist arrives hundreds of milliseconds after the heart beats. The speed at which this pulse wave travels (the pulse wave velocity (PWV)) is related to the stiffness of the arteries (i.e., PWV increases with increasing stiffness). Arterial stiffness is a known cardiovascular risk factor, and has been correlated with hypertension, heart failure, kidney disease, and other cardiovascular conditions. Therefore, pulse wave velocity is a potentially informative metric for preventative and diagnostic care. PWV is may be calculated by measuring the time at which the pulse passes two sites (the pulse transit time (PTT)), measuring the distance between those sites, and dividing that distance by the PTT. The two sites can be the carotid artery in the neck and the femoral artery in the leg, and distance is may be measured externally, i.e. with a tape measure on the surface of the chest.

With a wrist-worn device, the pulse transit time between the heart and the radial artery may be calculated by determining when the pressure wave left the heart and when the pressure wave arrived at the wrist. The PWV may then be calculated by dividing the distance from the heart to the wrist by the calculated PTT. The distance between the heart and the wrist may be calculated in any suitable manner.

Figure 3:
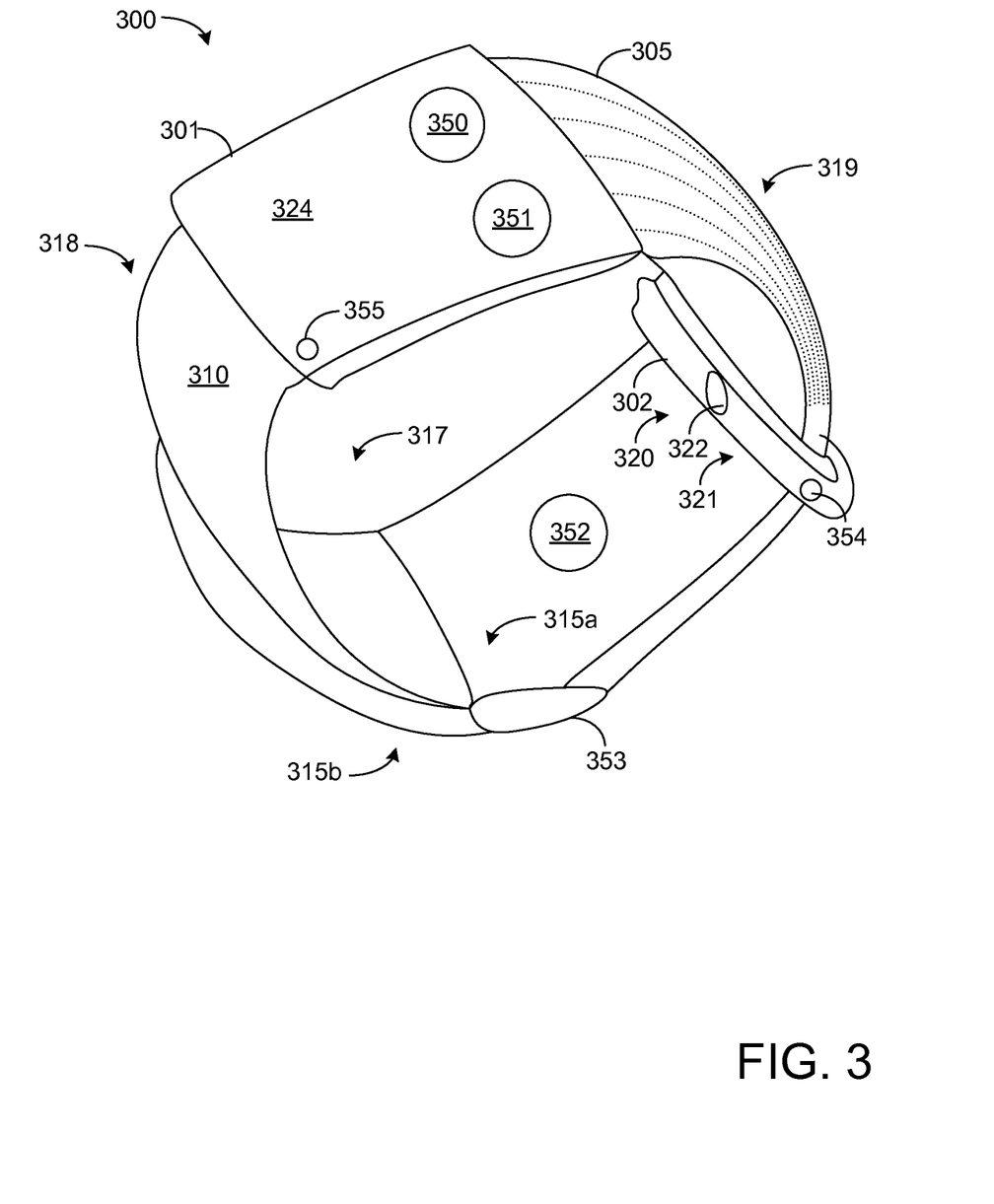
FIG. 3 shows a wrist-worn electronic device comprising multiple electrodes.

FIG. 3 shows an example wrist-worn device 300 that may be used to determine a pulse transit time of an individual wearing the device. Wrist-worn device 300 may be equipped with any of the features described above with reference to wearable electronic device 10. Wrist-worn device 300 includes a primary device 301, a satellite device 302, a first strap 305, and a second strap 310. Straps 305 and 310 each have one terminus at primary device 301. Fastening componentry 315a and 315b are located at the opposite termini of straps 310 and 305, respectively. The straps and fastening componentry enable the wearable pressure sensor to be closed into a loop and to be worn on a wearer's wrist. When closed into a loop, wrist-worn device 300 includes an inner surface 317 (user-adjacent side) and an outer surface 318 (externally-facing side). First strap 305 includes embedded conductive wires 319 that allow communication between and electrical coupling of primary device 301 and satellite device 302.

Satellite device 302 includes a pulse sensor assembly 320. In this example, pulse sensor assembly 320 will be described as a radial pressure pulse sensor (radial tonometer), but in other examples, an optical pulse sensor may be used. Additionally or alternatively, an optical pulse sensor may be included in primary device 301, first strap 305, and/or second strap 310. Pulse sensor assembly 320 includes pressure transducer assembly 321. A flexible cap 322 at least partially protrudes from the housing of satellite device 302 on inner surface 317 such that the flexible cap may be in contact with the skin of a wearer when wrist-worn device 300 is worn. Pressure applied to the flexible cap may then be conducted to a pressure transducer within pressure transducer assembly 321. In particular, when the flexible cap is positioned over the radial artery of a wearer, radial pulse-pressure waves may be conducted to the pressure transducer.

Satellite device 302 may be attached to first strap 305 at a fixed position, thus establishing a fixed distance between primary device 301 and satellite device 302. Fastening componentry 315a and 315b are complementary, and thus may be adjustably engaged to adjust the circumference of wrist-worn device 300 without moving the fixed position of the satellite device relative to the primary device. First strap 305 and/or second strap 310 may thus comprise an adjustable strap configured to fix a position of the satellite device relative to the primary device. The primary device, satellite device, and adjustable strap thus cooperatively form a loop configured to be worn around the wearer's wrist.

Primary device 301 includes display device 324, which may be used to output information regarding the wearer's pulse rate, blood pressure, and additional cardiovascular metrics, along with other information. As described for wearable electronic device 10, primary device 301 may further comprise other actuators that may be utilized to communicate with the wearer, such as a haptic motor, a loudspeaker, and one or more LEDs separate from display device 324.

Primary device 301 includes contact sensor modules 350 and 351 situated on the outer surface of device 300, which may be touchable by a wearer using fingers on the hand opposite the wrist where the device is worn, or may be placed in contact with other locations on the body of the wearer. The contact sensor modules may include independent or cooperating electrodes which may provide an electrical resistance and/or capacitance sensory function, which measures the electrical resistance and/or capacitance of the wearer's skin. In some examples, one of contact sensor modules 350 and 351 may be used as a ground electrode. The ground electrode may be pre-determined, or may vary based on application.

An additional contact sensor module 352 is shown located on the inner surface (user-adjacent) side of strap 305, which may contact the skin on the underside of the wearer's wrist while device 300 is worn and primary device 301 is located on the back of the wearer's wrist. Alternatively, contact sensor module 352 may be omitted, or may be placed on the inner surface of primary device 301 where it may contact the skin on the back of the wearer's wrist, or may be placed elsewhere along first strap 305 or second strap 310, provided conductive wires are embedded therein.

When included, contact sensor module 352, or an equivalent contact sensor module located on the inner surface of device 300 may thus function as a first electrode contacting a first measurement location on a wearer's skin, while contact sensor modules 350 and/or 351 may function as a second electrode that may contact a second measurement location on a wearer's skin. When the first measurement location is located on a first effective side of the wearer's heart and the second measurement location is located on a second effective side of the wearer's heart, a controller may be configured to measure an electrical potential between the first measurement location and the second measurement location. As described with reference to FIG. 2, the left arm and right arm of a wearer comprise Lead 1 of an EKG. As such, when a wearer touches contact sensor modules 350 and/or 351 with skin of the non-wearing hand or arm, a voltage difference across the wearer's heart may be determined.

One or more contact sensor modules (e.g., contact sensor module 353) additionally or alternatively may be located on an outer surface of device 300, such as on the externally-facing side of satellite device 302. Contact sensor module 353 may also be made from a conductive material and connected to conductive wires 319, or otherwise electrically coupled to primary device 301. In some examples, contact sensor module 353 may be attached to an exposed end of one or more conductive wires 319 via a screw, soldering, welding, etc. In the illustrated example, the contact sensor module is in the form of a buckle that is configured to couple first strap 305 and second strap 310 together (e.g., a component of fastening componentry 315a and 315b).

Due to the kinematic restraints of the wrist, it may be easier to contact some measurement locations (e.g. EKG leads) with contact sensor module 353 than with contact sensor modules 350 and 351. Contact sensor module 353 may also be used as a third electrode which may be placed in contact with other measurement locations on the body of the wearer, for example, measurement locations on a third effective side of the wearer's heart, opposite one or more of the first and second effective sides of the wearer's heart contacted by contact sensor modules 350, 351, and/or 352 (discussed further herein with reference to FIG. 5A). Additional ground electrodes may be located adjacent to contact sensor module 352 and/or contact sensor module 353. Alternatively, contact sensor module 353 may be divided into a conductive side and a ground side separated by an insulating layer.

Wrist-worn device 300 further comprises microphone 354 and camera 355. Microphone 354 is shown as part of satellite device 302, while camera 355 is shown as part of primary device 301. However, in other examples, the microphone and/or camera may be positioned in other locations on wrist-worn device 300. In still other examples, one or both of the microphone and the camera may be omitted. Camera 355 may be an infrared, color, stereoscopic, and/or depth camera. Wrist-worn device 300 may further include one or more motion sensors, such as accelerometers and gyroscopes.

Figures 4A, 4B:
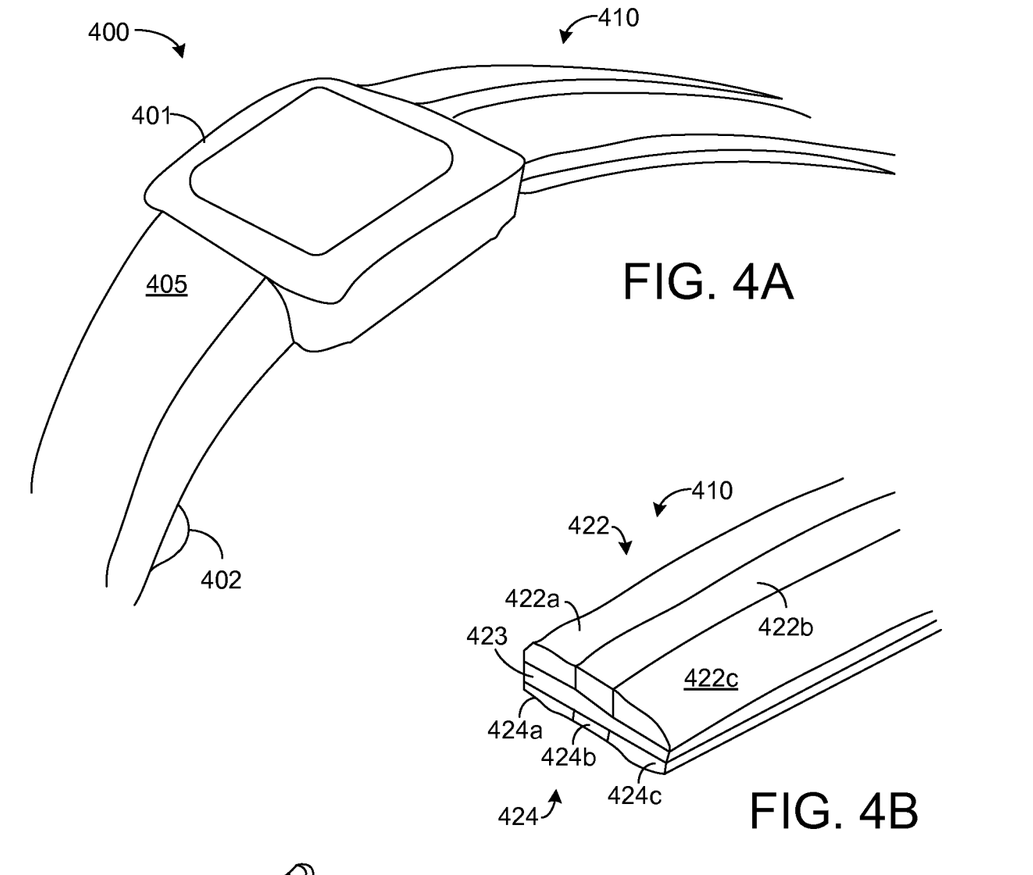
FIG. 4A-4C show a wrist-worn electronic device comprising a conductive strap.
Figure 4C:
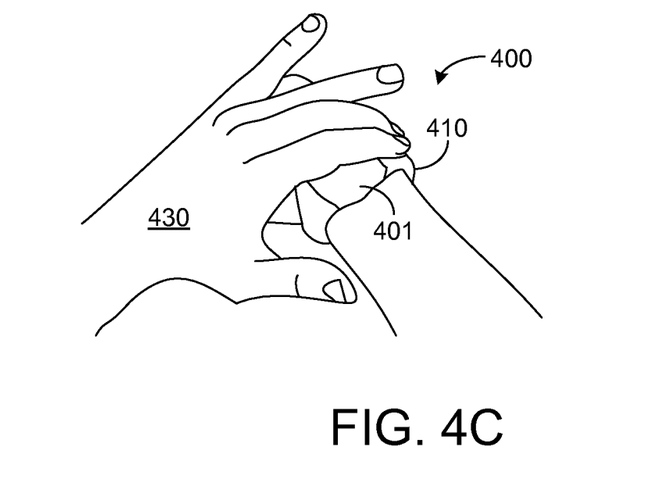

FIGS. 4A-4C show another wrist-worn device 400 that includes a primary device 401, a satellite device 402, a first strap 405 and a second strap 410. In addition to or as an alternative to the discreet contact sensors shown for wrist-worn device 300, first strap 405 and/or second strap 410 may be fabricated at least in part from a conductive elastomer that includes one or more conductive zones. The conductive elastomer may be electrically connected to primary device 401 and/or satellite device 402 via one or more conductive (e.g., metal) connection points, such as a watch-pin dowel, or a wire embedded in the strap during the fabrication process. Such a wire may emerge from the conductive elastomeric band for electrical connection with the primary and/or satellite device with intact insulation, while the portions of the wire embedded within the conductive elastomer may be stripped of insulation to promote electrical contact between the wire and the conductive elastomer.

FIG. 4B shows a cut-away view of second strap 410. Second strap 410 comprises three layers: outer layer 422, central layer 423, and inner (user-adjacent side) layer 424. Outer layer 422 may comprise three electrically-isolated conductive zones: 422a, 422b, and 422c. For example, zones 422a and 422c may be positive and negative electrodes, while zone 422b may be a ground electrode. However, many configurations are possible. In another example, one zone may be a conductive electrode, a second zone may be a ground electrode, and the third zone may be an insulated (e.g., non-conductive) zone. Instructive markings may be printed or molded onto the outside of the outer layer 422, indicating which zones the wearer should touch for a given application. Additionally or alternatively, instructions may be communicated to the wearer via a display device, a loudspeaker, and/or additional LEDs, etc. As shown in FIG. 4C, rather than touching individual contacts on wrist-worn device 400, wearer 430 may simply touch strap 410. Where wrist-worn device 400 includes a contact sensor module located on the inner surface, the inner surface contact sensor module may function as a first electrode, and a conductive zone on the outer layer of strap 410 may function as a second electrode.

Central layer 423 may be a conductive layer configured to transmit information and power between strap 410 and primary device 401 and/or satellite device 402. Additionally or alternatively, central layer 423 may provide conductive contacts between primary device 401 and satellite device 402.

Similarly to outer layer 422, inner layer 424 may comprise three conductive zones: 424a, 424b, and 424c, which may each be configured as positive or negative conductive electrodes, ground electrodes, or non-conductive zones. As inner layer 424 is in continuous contact with the skin of wearer 430, electrical information of the wearer may be taken continuously.

The wrist-worn devices of FIGS. 1, 3, and 4A-4C may thus comprise dry EKG electrodes. Typical EKG electrodes are either covered in conductive gel and/or made from conductive metal. Neither is suitable for continuous use in a wrist-worn device. In some embodiments the electrodes may be capacitive electrodes that may be able to transmit electrical signals through clothing. For example, contact sensor module 353, or other electrodes configured to contact with EKG leads on the chest may be capacitive.

The wearable nature of these electrodes makes it practical to respond quickly to a prompt from the wrist-worn device for an EKG measurement, and/or in response to symptoms, without retrieving a separate device. In some examples, a measurement may be taken without necessitating the wearer to put down any objects held in either hand.

In the examples shown in FIGS. 3 and 4A-4C, the wrist-worn device has one or more electrodes that contact the wearing wrist. If the device is worn on the right hand, for example, the wrist-contacting electrode is the right arm electrode (RA). A second electrode, such as contact sensor modules 350/351 or strap 410 may be touched by the wearer's left hand, as shown in FIG. 4C, thus providing a left arm electrode (LA). As shown in FIG. 2, this completes Lead I of an EKG circuit.

Figure 5A:
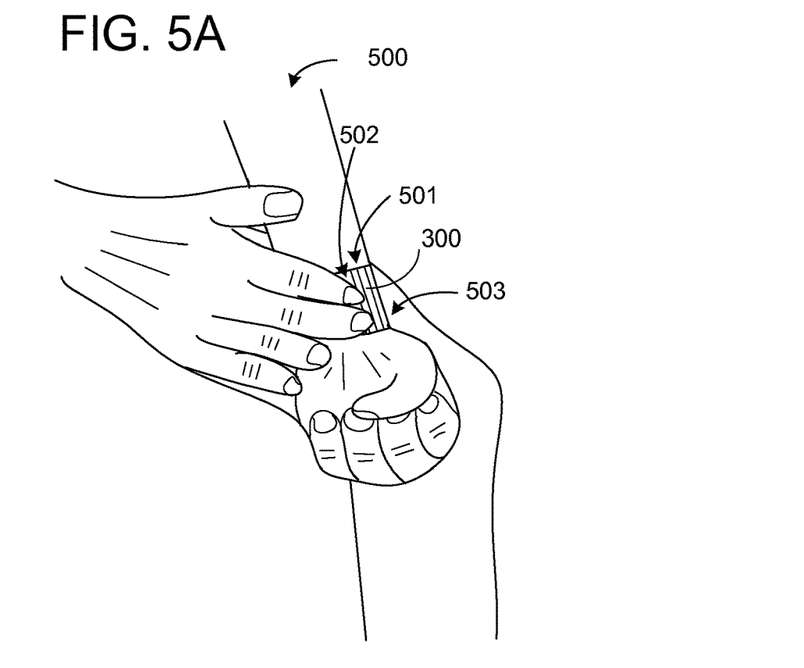
FIG. 5A shows a wearer engaging electrodes of a wrist-worn electronic device with a right hand, left hand, and left leg.

Using the example wrist-worn device shown in FIG. 3, contact sensor modules 350/351, 352, and 353 may be simultaneously contacted by the right arm, left arm, and left leg of the wearer to determine leads I, II, III, aVR, aVL, and aVF. FIG. 5A shows a wearer 500 wearing wrist-worn device 300 in a position to contact three EKG electrode placement locations (501, 502, and 503), and thus determine the six limb-leads. This information thus establishes a composite negative pole, which may then be used as the negative pole for the precordial leads V1-V6. As described with reference to FIG. 2, the precordial leads may then be determined using a single, unipolar electrode.

Figure 5B:
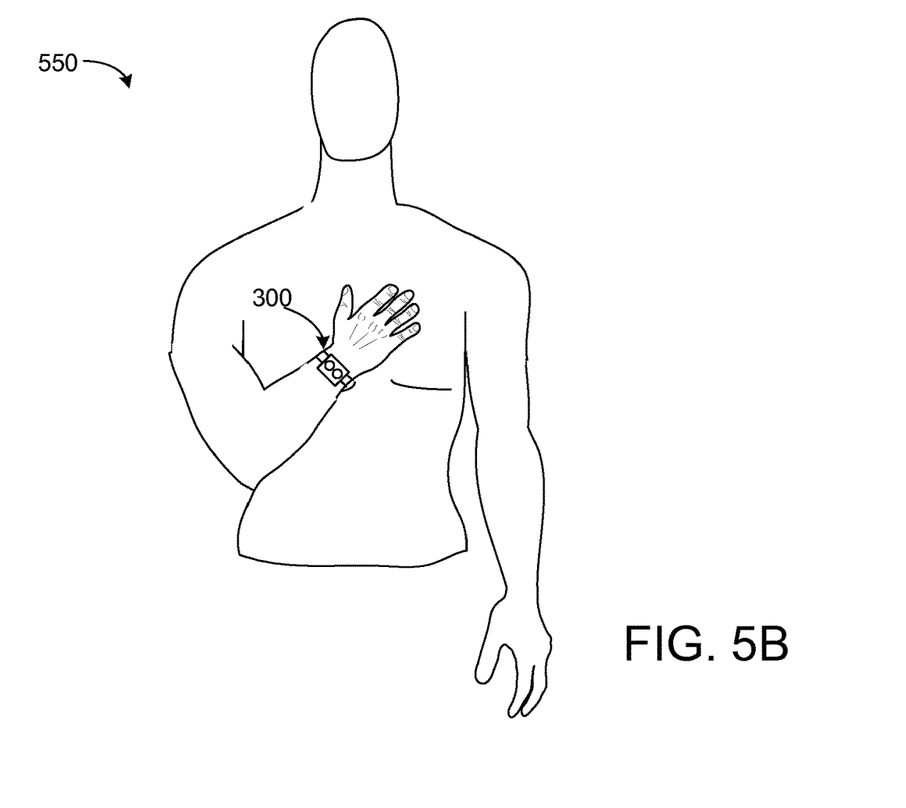
FIG. 5B shows a wearer engaging electrodes of a wrist-worn electronic device with a right hand and chest.

FIG. 5B shows a wearer 550 wearing wrist-worn device 300 in a position to establish the V1 precordial lead. Contact sensor module 353 (not visible) is placed against the chest between the fourth and fifth ribs to the right of the sternum. Wearer 550 may then move the position of contact sensor module 353 to provide leads V2-V6 in succession. The position of contact sensor module 353 relative to the chest of wearer 550 may be determined through sensors, such as motion sensors and/or camera 355, or through electrical feedback transmitted from the wearer. Such sensor information may be considered with understanding of mechanical constraints of the human body (e.g., limb length and joint angle). For example, a device may be trained to recognize sensor (e.g., accelerometer) measurements corresponding to correct device placement. In order to assist the wearer with placing contact sensor module 353, wrist-worn device 300 may provide feedback or instructions to the wearer via display device 324, a haptic motor, a loudspeaker, and/or one or more LEDs separate from the display device.

In some examples, a wearer may position an external camera directed at themself, such as a camera included in a smartphone, tablet computer, gaming device, or desktop computer. The external camera may communicate with the wrist-worn device 300 to improve placement of contact sensor module 353. In examples where the external camera is included in a computing device that also includes a display device, the display device may provide visual instructions for the wearer. In one example, electrode positions may be superimposed on a video image of the wearer on the display device, thus allowing the wearer to line up contact sensor module 353 to lead positions as if they were looking into a mirror. These methods for wearer feedback may also be used in conjunction with devices that include two sensors on the outer surface of the device (e.g., contact sensor modules 350 and 351) but do not include sensors on the user-adjacent of the device (e.g., contact sensor module 352 is omitted). By iteratively placing the two electrodes around the chest, different EKG leads may be provided over time.

With a user-adjacent contact sensor as a first electrode contacting a first measurement location on a first effective side of a wearer's heart, a wrist-worn heart monitoring device may include an electrode-positioning sensor subsystem to determine a three-dimensional position of a second electrode (e.g., contact sensor module 353) respective to a second measurement location. A controller may be configured to receive a voltage difference from the first and second electrodes and to receive an indication of the three-dimensional position of the second electrode respective to the second measurement location, the voltage difference indicative of an electrical potential of the wearer's heart. If the second electrode is located within a threshold distance of the second measurement location, the controller may output an electrical potential of the wearer's heart, and a user interface may communicate the electrical potential of the wearer's heart. However, if the second electrode is located more than a threshold distance from the second measurement location, the user interface may communicate an instruction to adjust the three-dimensional position of the second electrode.

Once an electrical potential has been determined at the second measurement location, the user interface may communicate an instruction to adjust the three-dimensional position of the second electrode from the second measurement location to a third measurement location. As per the second measurement location, the controller may be configured to receive an indication of the three-dimensional position of the second electrode respective to the third measurement location. If the second electrode is located within a threshold distance of the third measurement location, the controller may output an electrical potential of the wearer's heart, and a user interface may communicate the electrical potential of the wearer's heart. However, if the second electrode is located more than a threshold distance from the third measurement location, the user interface may communicate an instruction to adjust the three-dimensional position of the second electrode. This process may be iterated for a plurality of measurement locations. For example, multiple leads of an EKG may be determined in this manner.

As described herein, combining EKG measurements with pulse measurements at the wrist (e.g., radial artery pulse-pressure waves) may enable the determination of pulse transit time (PTT) and pulse wave velocity (PWV). However, this calculation benefits from one additional variable. The electrical information obtained via the EKG measurements indicate when the SA node outputs an electrical signal commanding the heart to contract and force blood out. However, the command signal is delayed as it passes through the AV node, in order to allow time for the heart muscle to build up enough pressure to open the valves and force blood and the accompanying pressure wave out into the aorta. This period, which may take from tens to hundreds of milliseconds—while pressure is building up in the left ventricle but the aortic valve is still closed—is known as the pre-ejection period (PEP). In order to accurately determine PTT, and thus PWV, one needs to know when the pressure wave actually left the heart. Without this information, the EKG signal and radial artery pressure signal can only yield the radial pulse arrival time (PAT), which is not as clinically informative.

To determine when the pressure wave leaves the heart, a phonocardiogram (PCG) may be used. A PCG measures sounds produced by the heart by placing a microphone (e.g., microphone 354) against the chest or back of an individual. The PCG is often used to look for atypical heart sounds, indicating valve abnormalities, for example. In addition, the PCG can also indicate the exact time at which the aortic valve closes, which is also visible in the pressure wave observed at the radial artery. Indeed, the PTT may be estimated based solely on the PCG and pulse measurements at the wrist, based on the duration between the audible sound of the aortic valve closing and the appearance of a dicrotic notch in the pulse pressure wave. Furthermore, the pulse pressure wave may be analyzed to determine an estimated time between the aortic valve opening and closing, and this estimated time may be subtracted from the valve closing recognized by the microphone to yield the estimated time of aortic valve opening. By calibrating the estimated time of aortic valve opening to the time of the command signal, the PTT and PWV subsequently may be determined based only on the EKG and pulse pressure wave signals, allowing for PTT and PWV monitoring without requiring a wearer to hold a microphone to their chest once calibrated.

Returning to FIG. 5B, when wearer 550 places contact sensor module 353 against their chest, microphone 354 is also brought close to the chest. Microphone 354 may thus transmit an audio signal which may indicate the timing of the aortic valve closing. The closing of the aortic valve is also discernable from the pulse pressure wave signal (dicrotic notch). Thus, by combining pressure sensing at the wrist, PCG, and EKG, the duration of the PEP can be determined, and thus an accurate PTT and PWV may also be determined. For most individuals, the PEP is relatively stable and consistent between heart beats. As such, the PCG may not need to be recorded every time a PTT and PWV are determined. Indeed, the radial pulse wave and an EKG signal taken from Lead I may be sufficient to determine a current PTT once an initial PTT has been calibrated to the PAT based on the PEP. Thus, once calibrated, a current PTT may be determined without placing the wrist-worn device to the chest. In some implementations, the PWV may be determined using a PEP that varies as a function of a measured heart rate (e.g., PEP decreases with increasing heart rate). Such a function may be estimated based on general population data. Alternatively, a function can be built for a particular wearer based on a series of PEP measurements at different heart rates.

Figure 6:
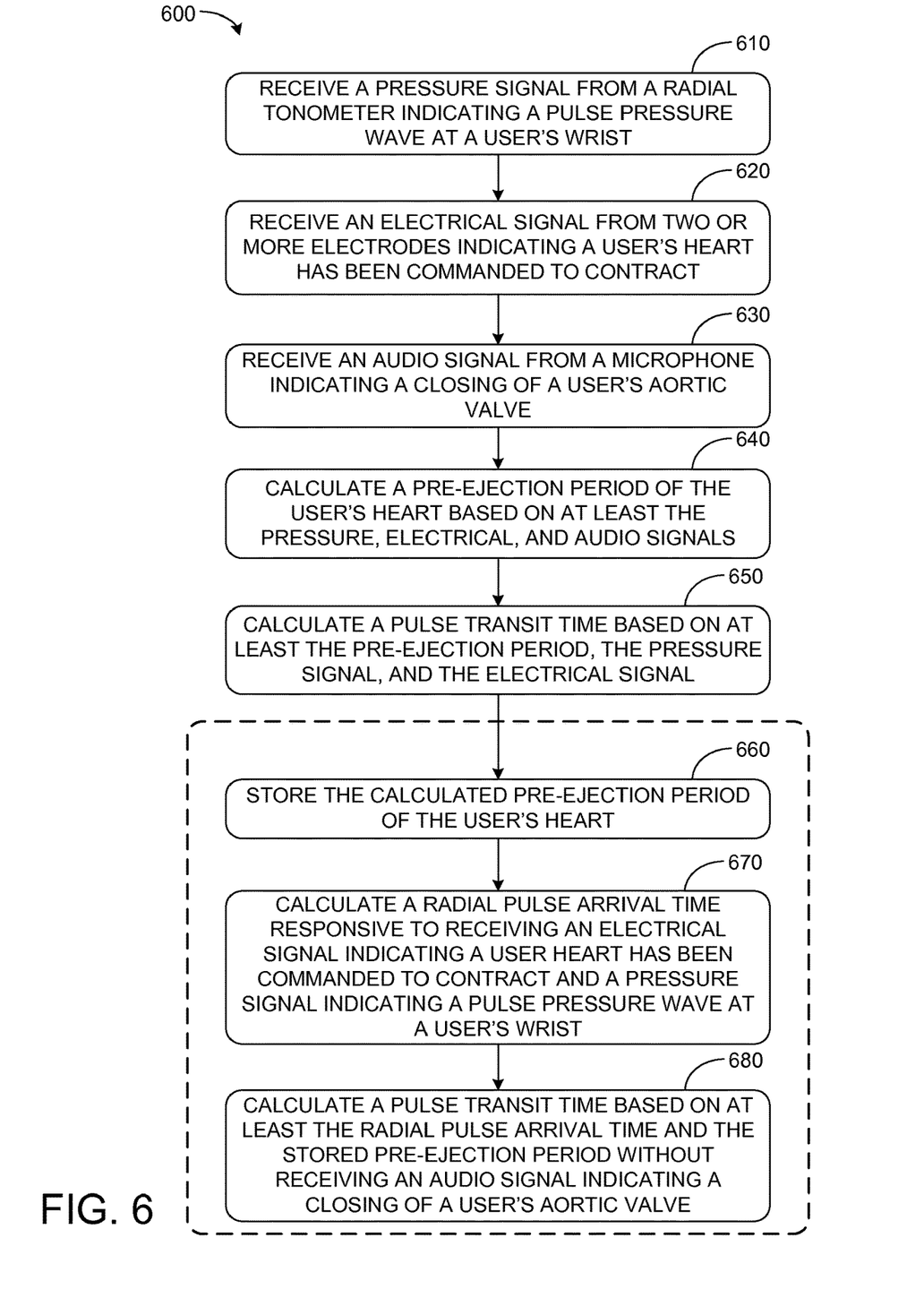
FIG. 6 shows an example method for determining a pulse transit time with a wrist-worn device.

FIG. 6 shows a flow chart for an example method 600 for determining pulse-transit time with a wrist-worn device, for example wrist-worn device 300. As described herein, the wrist-worn device may include a radial tonometer configured to output a pressure signal indicating a pulse pressure wave at a wearer's wrist, two or more electrodes configured to output an electrical signal indicating a wearer's heart has been commanded to contract, and a microphone configured to output an audio signal indicating a closing of a wearer's aortic valve. Method 600 may be implemented by way of a pulse transit time monitor, which may be included in a compute device of the wrist-worn device.

At 610, method 600 includes receiving a pressure signal from a radial tonometer indicating a pulse pressure wave at a wearer's wrist. Continuing at 620, method 600 includes receiving an electrical signal from two or more electrodes indicating a wearer's heart has been commanded to contract. The electrical signal may be based on an electrical potential between a first measurement location on a wearer's skin on a first effective side of the wearer's heart, and a second measurement location on a wearer's skin on a second, opposite, effective side of the wearer's heart. The electrical signal may be output responsive to a sensed heartbeat command while a first electrode contacts the first measurement location and a second electrode contacts the second measurement location.

Continuing at 630, method 600 includes receiving an audio signal from a microphone indicating a closing of a wearer's aortic valve. At 640, method 600 includes calculating a pre-ejection period of the wearer's heart based on at least the pressure, electric, and audio signals. In other words, the interval between the commanded heart contraction (as measured by the electrical signal), and the aortic valve opening is calculated based on the time of the closing of the aortic valve (as measured by the audio signal) and the estimated period between the valve opening and closing measured between a forward pressure wave arrival and a dicrotic notch in the pressure signal. At 650, method 600 includes calculating a pulse transit time based on at least the pre-ejection period, the pressure signal, and the electrical signal. Method 600 may further include calculating a pulse wave velocity based on the pulse transit time and a distance between the wearer's aortic valve and the wearer's wrist.

Optionally, method 600 may continue to 660, where the method may include storing the calculated pre-ejection period of the wearer's heart. Continuing at 670, method 600 may include calculating a radial pulse arrival time responsive to receiving an electrical signal indicating the wearer's heart has been commanded to contract, a pressure signal indicating a pulse pressure wave at the wearer's wrist. The pressure signal may indicate a forward pressure wave arrival at the wearer's wrist. Continuing at 680, method 600 may further include calculating a pulse-transit time based on at least the radial pulse arrival time and the stored pre-ejection period without receiving an audio signal indicating a closing of the wearer's aortic valve. A pulse wave velocity may then be calculated based on the pulse transit time and the distance between the wearer's aortic valve and the wearer's wrist.

As evident from the foregoing description, the methods and processes described herein may be tied to a sensor-and-logic system of one or more machines. Such methods and processes may be implemented as a computer-application program or service, an application-programming interface (API), a library, firmware, and/or other computer-program product. FIG. 1 shows one, non-limiting example of a sensor-and-logic system to enact the methods and processes described herein. However, these methods and process may also be enacted on sensor-and-logic systems of other configurations and form factors, as shown schematically in FIG. 7.

Figure 7:
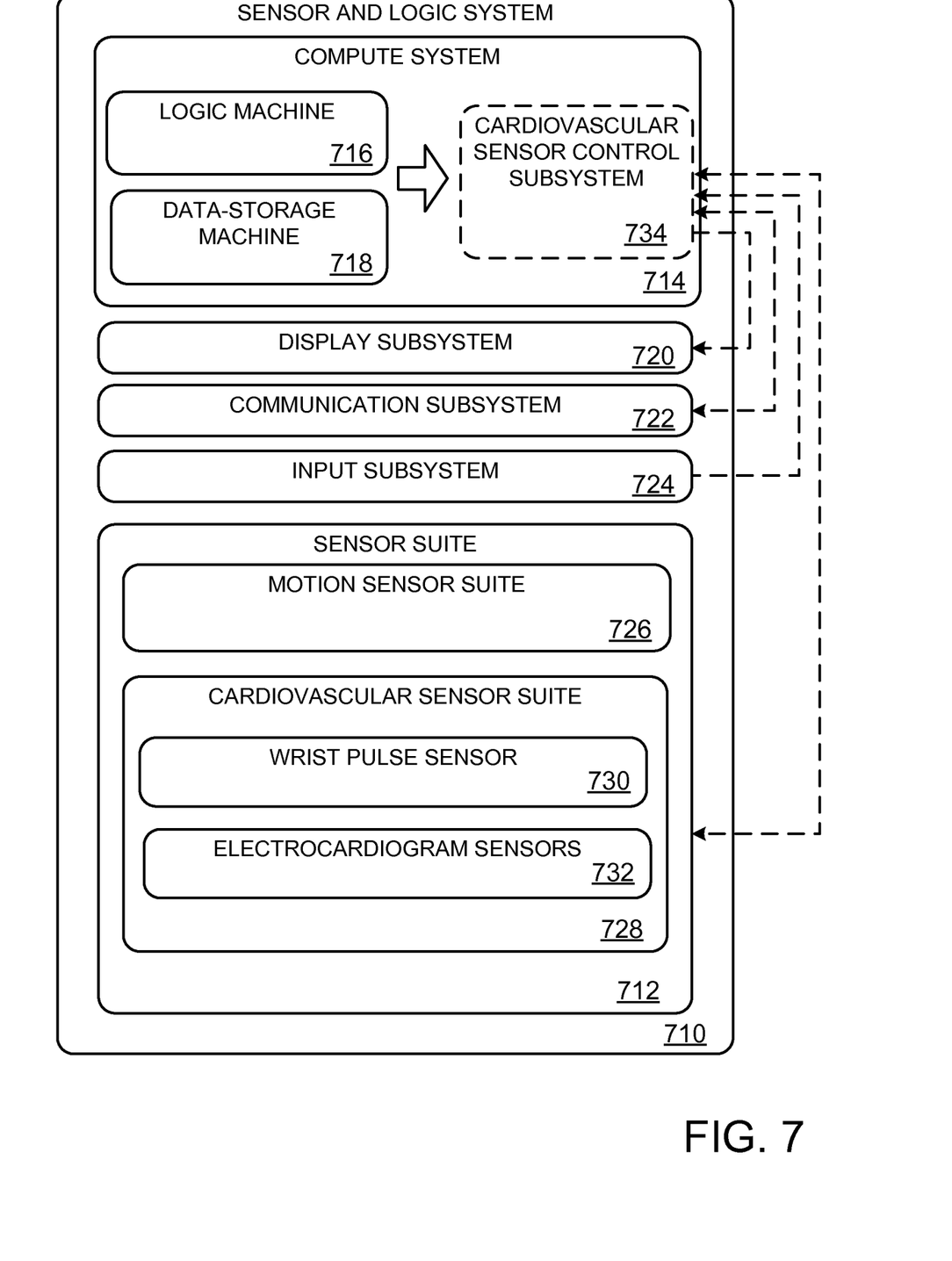
FIG. 7 schematically shows a sensor-and-logic system usable to determine a pulse transit time with a wrist-worn sensor.

FIG. 7 schematically shows a form-agnostic sensor-and-logic system 710 that includes a sensor suite 712 operatively coupled to a compute system 714. The compute system includes a logic machine 716 and a data-storage machine 718. The compute system is operatively coupled to a display subsystem 720, a communication subsystem 722, an input subsystem 724, and/or other components not shown in FIG. 7.

Logic machine 716 includes one or more physical devices configured to execute instructions. The logic machine may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

Logic machine 716 may include one or more processors configured to execute software instructions. Additionally or alternatively, the logic machine may include one or more hardware or firmware logic machines configured to execute hardware or firmware instructions. Processors of the logic machine may be single-core or multi-core, and the instructions executed thereon may be configured for sequential, parallel, and/or distributed processing. Individual components of a logic machine optionally may be distributed among two or more separate devices, which may be remotely located and/or configured for coordinated processing. Aspects of a logic machine may be virtualized and executed by remotely accessible, networked computing devices in a cloud-computing configuration.

Data-storage machine 718 includes one or more physical devices configured to hold instructions executable by logic machine 716 to implement the methods and processes described herein. When such methods and processes are implemented, the state of the data-storage machine may be transformed—e.g., to hold different data. The data-storage machine may include removable and/or built-in devices; it may include optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. The data-storage machine may include volatile, nonvolatile, dynamic, static, read/write, read-only, random-access, sequential-access, location-addressable, file-addressable, and/or content-addressable devices.

Data-storage machine 718 includes one or more physical devices. However, aspects of the instructions described herein alternatively may be propagated by a communication medium (e.g., an electromagnetic signal, an optical signal, etc.) that is not held by a physical device for a finite duration.

Aspects of logic machine 716 and data-storage machine 718 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

Display subsystem 720 may be used to present a visual representation of data held by data-storage machine 718. This visual representation may take the form of a graphical user interface (GUI). As the herein described methods and processes change the data held by the storage machine, and thus transform the state of the storage machine, the state of display subsystem 720 may likewise be transformed to visually represent changes in the underlying data. Display subsystem 720 may include one or more display subsystem devices utilizing virtually any type of technology. Such display subsystem devices may be combined with logic machine 716 and/or data-storage machine 718 in a shared enclosure, or such display subsystem devices may be peripheral display subsystem devices. Display 34 of FIG. 1 is an example of display subsystem 720.

Communication subsystem 722 may be configured to communicatively couple compute system 714 to one or more other computing devices. The communication subsystem may include wired and/or wireless communication devices compatible with one or more different communication protocols. As non-limiting examples, the communication subsystem may be configured for communication via a wireless telephone network, a local- or wide-area network, and/or the Internet. Communication suite 36 of FIG. 1 is an example of communication subsystem 722.

Input subsystem 724 may comprise or interface with one or more user-input devices such as a keyboard, touch screen, button, dial, joystick, or switch. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition. Push button 48 of FIG. 1 is an example of input subsystem 724.

Sensor suite 712 may include one or more different sensors—e.g., a touch-screen sensor, push-button sensor, microphone, visible-light sensor, ultraviolet sensor, ambient-temperature sensor, contact sensors, and/or GPS receiver—as described above with reference to FIG. 1. Sensor suite 712 may include motion sensor suite 726 and cardiovascular sensor suite 728. Motion sensor suite 726 may include one or more of an accelerometer, gyroscope, magnetometer, or other suitable motion detectors.

As described herein, cardiovascular sensor suite may include wrist pulse sensor 730 and electrocardiogram sensors 732, as well as one or more microphones. Compute system 714 may include cardiovascular sensor control subsystem 734, which may be communicatively coupled to logic machine 716 and data-storage machine 718, as well as sensor suite 712. Wrist pulse sensor 730 may include a pressure transducer comprising one or more piezo-resistive sensors configured to provide absolute pressure signals to compute system 714 via an analog-to-digital converter. Such a pressure transducer may be configured to transduce pressure waves from the radial artery through the skin of the wearer. Wrist pulse sensor 730 may additionally or alternatively include an optical pulse sensor. An optical pulse sensor may comprise an optical source, such as one or more LED emitters, for example, and may further comprise an optical sensor including one or more photodiodes matched to detect light at frequencies that are based on the frequencies of light output by the optical source. The optical source may be configured to illuminate one or more blood vessels through the skin of the wearer, and the optical sensor may be configured to measure illumination reflected from or transmitted through blood vessels.

Electrocardiogram sensors 732 may include one or more contact sensor modules that may include independent or cooperating sensor elements. The contact sensor modules may provide an electrical resistance and/or capacitance sensory function, which measures the electrical resistance and/or capacitance of the wearer's skin. Electrocardiogram sensors 732 may provide absolute resistance and/or capacitance signals to compute system 714 via an analog-to-digital converter.

Cardiovascular sensor control subsystem 734 may further receive raw signals from one or more microphones, cameras, accelerometers, gyroscopes, other components of sensor suite 712, as well as raw and/or pre-processed signals received from components of input subsystem 724, and raw and/or pre-processed signals received from components of communication subsystem 722. Cardiovascular sensor control subsystem 734 may process the raw and/or pre-processed signals to determine heart rate, blood pressure, caloric expenditures, pulse transit time, pulse wave velocity, heart pre-ejection period, radial pulse arrival time, etc. Processed signals may be stored and output via compute system 714. Control signals sent to sensor suite 712 may be based on signals received from sensor suite 712, information stored in data-storage machine 718, input received from communication subsystem 722, input received from input subsystem 724, etc. Processed signals may be transmitted via display subsystem 720 and/or communication subsystem 722. As described herein, cardiovascular sensor control subsystem 734 may include a plurality of subsystems, such as a pulse-transit time monitor, an electrode-positioning sensor subsystem, one or more controllers, and one or more user interfaces.

In an example, a wrist-worn heart monitoring device comprises: a radial tonometer configured to output a pressure signal indicating a pulse pressure wave at a wearer's wrist; two or more electrodes configured to output an electrical signal indicating a wearer's heart has been commanded to contract; a microphone configured to output an audio signal indicating a closing of a wearer's aortic valve; and a pulse transit time monitor configured to: calculate a pre-ejection period of the wearer's heart based on at least the pressure, electrical, and audio signals; and calculate a pulse transit time based on at least the pre-ejection period, the pressure signal, and the electrical signal. In this example or any other example, one or more electrodes are located on a user-adjacent surface of the wrist-worn heart monitoring device, and one or more electrodes are located on an externally-facing surface of the wrist-worn heart monitoring device. In this example or any other example, the device further comprises: a primary device; a satellite device including the radial tonometer; and an adjustable strap configured to fix a position of the satellite device relative to the primary device, the primary device, satellite device, and adjustable strap cooperatively forming a loop configured to be worn around the wearer's wrist. In this example or any other example, the radial tonometer further comprises: a flexible cap configured to at least partially protrude from an opening in a housing of the satellite device, and further configured to conduct pressure to a pressure transducer within the satellite device. In this example or any other example, one or more of the electrodes located on the externally-facing surface of the wrist-worn heart monitoring device are located at the adjustable strap. In this example or any other example, the electrical signal indicating a wearer's heart has been commanded to contract is output responsive to a sensed heartbeat command while first electrode contacts a first measurement location on a wearer's skin on a first effective side of the wearer's heart, and a second electrode contacts a second measurement location on the wearer's skin on a second, opposite, effective side of the wearer's heart. In this example or any other example, the pulse transit time monitor is further configured to: calculate a pulse wave velocity based on the pulse transit time and a distance between the wearer's aortic valve and the wearer's wrist. In this example or any other example, the pulse transit time monitor is further configured to: store the calculated pre-ejection period of the wearer's heart; and calculate a radial pulse arrival time responsive to receiving an electrical signal indicating the wearer's heart has been commanded to contract, and a pressure signal indicating a pulse pressure wave at the wearer's wrist; calculate a pulse-transit time based on at least the radial pulse arrival time and the stored pre-ejection period without receiving an audio signal indicating a closing of the wearer's aortic valve.

In an example, a wrist-worn heart monitoring device comprises: a primary device; an adjustable strap, the primary device and adjustable strap cooperatively forming a loop configured to be worn around a wearer's wrist, the loop having an inner surface facing the wearer's wrist and an outer surface facing away from the wearer's wrist; a first electrode on the inner surface of the loop and configured to contact a first measurement location on a wearer's skin on a first effective side of the wearer's heart; a second electrode on the outer surface of the loop at the adjustable strap and configured to contact a second measurement location on the wearer's skin on a second, opposite, effective side of the wearer's heart; and a controller configured to measure an electrical potential between the first measurement location and the second measurement location. In this example or any other example, the first electrode is in contact with an underside of the wearer's wrist when the primary device is located on a back of the wearer's wrist. In this example or any other example, the adjustable strap comprises one or more conductive zones on an outer surface of the adjustable strap, and the second electrode is included in a conductive zone on the outer surface of the adjustable strap. In this example or any other example, the adjustable strap comprises one or more conductive zones on an inner surface of the adjustable strap, and the first electrode is included in a conductive zone on the inner surface of the adjustable strap. In this example or any other example, the device further comprises: a third electrode on the outer surface of the loop and configured to contact a third measurement location on the wearer's skin. In this example or any other example, the device further comprises: fastening componentry configured to adjust a circumference of the loop through interactions with the adjustable strap and including one or more conductive components electrically coupled to the primary device such that the third electrode comprises the one or more conductive components of the fastening componentry. In this example or any other example, the controller is further configured to determine a composite negative pole of the wearer based on the electrical potential between the first measurement location and the second measurement location, an electrical potential between the first measurement location and the third measurement location, and an electrical potential between the second measurement location and the third measurement location.

In an example, a wrist-worn heart monitoring device comprises: a first electrode and a second electrode, the first and second electrodes configured to output a voltage difference indicative of an electrical potential of a wearer's heart when the first electrode contacts a first measurement location on a wearer's skin on a first effective side of the wearer's heart and the second electrode contacts a second measurement location on the wearer's skin on a second, opposite, effective side of the wearer's heart; an electrode-positioning sensor subsystem to determine a three-dimensional position of the second electrode respective to the second measurement location; and a controller configured to: receive a voltage difference from the first and second electrodes; receive an indication of the three-dimensional position of the second electrode respective to the second measurement location from the electrode-positioning sensor subsystem; and output an electrical potential of the wearer's heart responsive to the second electrode being located within a threshold distance of the second measurement location. In this example or any other example, the device further comprises a user interface configured to: communicate an instruction to adjust the three-dimensional position of the second electrode responsive to the second electrode being located more than the threshold distance from the second measurement location. In this example or any other example, the electrode-positioning sensor subsystem is further configured to determine a three-dimensional position of the second electrode respective to one or more additional measurement locations, and the user interface is further configured to: communicate an instruction to adjust the three-dimensional position of the second electrode from the second measurement location to a third measurement location. In this example or any other example, the controller is further configured to: receive an indication of the three-dimensional position of the second electrode respective to the third measurement location from the electrode-positioning sensor subsystem; and output the electrical potential of the user's heart responsive to the second electrode being located within the threshold distance of the third measurement location. In this example or any other example, the electrode-positioning sensor subsystem is configured to receive signals from one or more motion sensors included in the wrist-worn heart monitoring device, and from one or more cameras.

The configurations and approaches described herein are exemplary in nature, and that these specific implementations or examples are not to be taken in a limiting sense, because numerous variations are feasible. The specific routines or methods described herein may represent one or more processing strategies. As such, various acts shown or described may be performed in the sequence shown or described, in other sequences, in parallel, or omitted.

The subject matter of this disclosure includes all novel and non-obvious combinations and sub-combinations of the various processes, systems and configurations, and other features, functions, acts, and/or properties disclosed herein, as well as any and all equivalents thereof.

The invention claimed is:

1. A wrist-worn heart monitoring device, comprising:
a primary device;
an adjustable strap, the primary device and adjustable strap cooperatively forming a loop configured to be worn around a wearer's wrist, the loop having an inner surface facing the wearer's wrist and an outer surface facing away from the wearer's wrist;
a first electrode on the inner surface of the loop and configured to contact a first measurement location on the wearer's skin on a first effective side of the wearer's heart;
a second electrode on the outer surface of the loop at the adjustable strap and configured to contact a second measurement location on the wearer's skin on a second, opposite, effective side of the wearer's heart;
a microphone positioned on the outer surface of the loop and configured to output an audio signal indicating a closing of the wearer's aortic valve;
a radial tonometer configured to output a pressure signal indicating a pulse pressure wave at the wearer's wrist;
a controller configured to measure an electrical potential between the first measurement location and the second measurement location; and
a pulse transit time monitor configured to:
  receive a first electrical signal from the first and second electrodes, wherein the first electrical signal is an electrocardiograph (ECG);
  receive a first audio signal from the microphone;
  receive a first pressure signal from the radial tonometer;
  calculate a pre-ejection period (PEP) of the wearer's heart, wherein the PEP is calculated as an elapsed time between a first identified timepoint in the ECG indicating a command to contract a left ventricle and a second identified time point indicating a timing of an aortic valve opening,
  wherein a third identified timepoint in the first audio signal indicates a timing of an aortic valve closing,
  wherein a total aortic valve opening period is determined by subtracting a fourth identified timepoint in the first pressure signal indicating the aortic valve opening from a fifth identified timepoint in the first pressure signal indicating the aortic valve closing, and
  wherein the second identified time point is determined by subtracting the total aortic valve opening period from the third identified timepoint,
  calculate a first pulse transit time based on at least the pre-ejection period, the first pressure signal, and the first electrical signal;
  store the calculated pre-ejection period of the wearer's heart;
  calculate a radial pulse arrival time responsive to receiving a second electrical signal indicating the wearer's heart has been commanded to contract, and a second pressure signal indicating the pulse pressure wave at the wearer's wrist; and
  calculate a second pulse transit time based on at least the radial pulse arrival time and the stored pre-ejection period without receiving a second audio signal indicating a closing of the wearer's aortic valve.

2. The wrist-worn heart monitoring device of claim 1, wherein the first electrode is configured to be in contact with an underside of the wearer's wrist when the primary device is located on a back of the wearer's wrist.

3. The wrist-worn heart monitoring device of claim 1, wherein the adjustable strap comprises one or more conductive zones on an outer surface of the adjustable strap, and wherein the second electrode is included in a conductive zone of the one or more conductive zones on the outer surface of the adjustable strap.

4. The wrist-worn heart monitoring device of claim 3, wherein the adjustable strap comprises one or more conductive zones on an inner surface of the adjustable strap, and wherein the first electrode is included in a conductive zone of the one or more conductive zones on the inner surface of the adjustable strap.

5. The wrist-worn heart monitoring device of claim 1, further comprising:
   a third electrode on the outer surface of the loop and configured to contact a third measurement location on the wearer's skin.

6. The wrist-worn heart monitoring device of claim 5, further comprising:
   fastening componentry configured to adjust a circumference of the loop through interactions with the adjustable strap and including one or more conductive components electrically coupled to the primary device such that the third electrode comprises the one or more conductive components of the fastening componentry.

7. The wrist-worn heart monitoring device of claim 5, wherein the controller is further configured to determine a composite negative pole of the wearer based on the electrical potential between the first measurement location and the second measurement location, an electrical potential between the first measurement location and the third measurement location, and an electrical potential between the second measurement location and the third measurement location.

8. The wrist-worn heart monitoring device of claim 1, further comprising:
   a satellite device including the radial tonometer, wherein the adjustable strap is configured to fix a position of the satellite device relative to the primary device.

9. The wrist-worn heart monitoring device of claim 1, wherein the pulse transit time monitor is further configured to:
   calculate a pulse wave velocity based on the pulse transit time and a distance between the wearer's aortic valve and the wearer's wrist.

10. A wrist-worn heart monitoring device, comprising:
   a primary device;
   an adjustable strap, the primary device and adjustable strap cooperatively forming a loop configured to be worn around a wearer's wrist, the adjustable strap having an inner surface facing the wearer's wrist and an outer surface facing away from the wearer's wrist, wherein the adjustable strap comprises:
      one or more conductive zones extending along a length of the inner surface of the adjustable strap, wherein a conductive zone of the one or more conductive zones on the inner surface of the adjustable strap functions as a first electrode configured to contact a first measurement location on the wearer's skin on a first effective side of the wearer's heart; and
      one or more conductive zones extending along a length of the outer surface of the adjustable strap, wherein a conductive zone of the one or more conductive zones on the outer surface of the adjustable strap functions as a second electrode configured to contact a second measurement location on the wearer's skin on a second effective side of the wearer's heart;
   a microphone positioned on the outer surface of the loop and configured to output an audio signal indicating a closing of the wearer's aortic valve;
   a radial tonometer configured to output a pressure signal indicating a pulse pressure wave at the wearer's wrist;
   a controller configured to measure an electrical potential between the first measurement location and the second measurement location; and
   a pulse transit time monitor configured to:
      receive a first electrical signal from the first and second electrodes, wherein the first electrical signal is an electrocardiograph (ECG);
      receive a first audio signal from the microphone;
      receive a first pressure signal from the radial tonometer;
      calculate a pre-ejection period (PEP) of the wearer's heart, wherein the PEP is calculated as an elapsed time between a first identified timepoint in the ECG indicating a command to contract a left ventricle and a second identified time point indicating a timing of an aortic valve opening,
         wherein a third identified timepoint in the first audio signal indicates a timing of an aortic valve closing,
         wherein a total aortic valve opening period is determined by subtracting a fourth identified timepoint in the first pressure signal indicating the aortic valve opening from a fifth identified timepoint in the first pressure signal indicating the aortic valve closing, and
         wherein the second identified time point is determined by subtracting the total aortic valve opening period from the third identified timepoint,
      calculate a first pulse transit time based on at least the pre-ejection period, the first pressure signal, and the first electrical signal;
   store the calculated pre-ejection period of the wearer's heart;
   calculate a radial pulse arrival time responsive to receiving a second electrical signal indicating the wearer's heart has been commanded to contract, and a second pressure signal indicating the pulse pressure wave at the wearer's wrist; and
   calculate a second pulse transit time based on at least the radial pulse arrival time and the stored pre-ejection period without receiving a second audio signal indicating a closing of the wearer's aortic valve.

* * * * *